US011278390B2

(12) United States Patent
Lostetter

(10) Patent No.: US 11,278,390 B2
(45) Date of Patent: Mar. 22, 2022

(54) STENT GRAFT WITH FENESTRATION LOCK AND METHODS OF USE

(71) Applicant: Bolton Medical, Inc., Sunrise, FL (US)

(72) Inventor: Timothy Lostetter, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 0 days.

(21) Appl. No.: 16/392,443

(22) Filed: Apr. 23, 2019

(65) Prior Publication Data

US 2019/0247179 A1 Aug. 15, 2019

Related U.S. Application Data

(63) Continuation of application No. PCT/US2018/019352, filed on Feb. 23, 2018.
(Continued)

(51) Int. Cl.
*A61F 2/02* (2006.01)
*A61F 2/07* (2013.01)
*A61F 2/06* (2013.01)
*A61F 2/82* (2013.01)
*A61F 2/848* (2013.01)

(52) U.S. Cl.
CPC .......... *A61F 2/07* (2013.01); *A61F 2002/061* (2013.01); *A61F 2002/067* (2013.01); *A61F 2002/075* (2013.01); *A61F 2002/821* (2013.01); *A61F 2002/8486* (2013.01); *A61F 2210/0014* (2013.01); *A61F 2220/0033* (2013.01); *A61F 2220/0075* (2013.01); *A61F 2250/006* (2013.01); *A61F 2250/0069* (2013.01)

(58) Field of Classification Search
CPC .................. A61F 2/07; A61F 2002/061; A61F 2002/067; A61F 2002/075; A61F 2002/821; A61F 2002/8486; A61F 2210/0014; A61F 2220/0033; A61F 2220/0075; A61F 2250/006; A61F 2250/0069
See application file for complete search history.

(56) References Cited

U.S. PATENT DOCUMENTS 5,123,917 A 6/1992 Lee
5,242,452 A 9/1993 Inoue
(Continued)

FOREIGN PATENT DOCUMENTS

CN 105832447 A 8/2016
EP 1847234 A1 10/2007
(Continued)

OTHER PUBLICATIONS

International Preliminary Report on Patentability for International Application No. PCT/US2018/019352 dated Aug. 27, 2019.
(Continued)

*Primary Examiner* — Erich G Herbermann
(74) *Attorney, Agent, or Firm* — Foley Hoag LLP

(57) ABSTRACT

A stent graft includes a luminal graft component defining at least one fenestration. At least one ligature traverses the fenestration and at least partially defines an opening within the fenestration that secures a branch prosthesis. The stent graft is implanted in a patient to thereby treat an arterial aneurysm, such as an aortic aneurysm in a region of the aorta that includes at least one arterial branch, including juxtarenal and short-neck aortic aneurysms.

13 Claims, 8 Drawing Sheets

Related U.S. Application Data

(60) Provisional application No. 62/463,054, filed on Feb. 24, 2017.

(56) References Cited

U.S. PATENT DOCUMENTS

| | | | |
|---|---|---|---|
| 5,507,769 A | 4/1996 | Marin et al. | |
| 5,713,948 A | 2/1998 | Uflacker | |
| 5,873,906 A | 2/1999 | Lau et al. | |
| 6,113,623 A * | 9/2000 | Sgro | A61B 17/0057 606/151 |
| 6,171,334 B1 | 1/2001 | Cox | |
| 6,280,464 B1 | 8/2001 | Hayashi | |
| 6,395,018 B1 | 5/2002 | Castaneda | |
| 7,435,253 B1 | 10/2008 | Hartley et al. | |
| 7,637,940 B2 | 12/2009 | Kocur et al. | |
| 7,763,063 B2 | 7/2010 | Arbefeuille et al. | |
| 8,007,605 B2 | 8/2011 | Arbefeuille et al. | |
| 8,062,345 B2 | 11/2011 | Ouellette et al. | |
| 8,172,895 B2 | 5/2012 | Anderson et al. | |
| 8,333,800 B2 | 12/2012 | Bruszewski et al. | |
| 8,480,725 B2 | 7/2013 | Rasmussen et al. | |
| 8,764,812 B2 | 7/2014 | Mayberry et al. | |
| 8,808,351 B2 | 8/2014 | Osborne | |
| 8,915,955 B2 | 12/2014 | West et al. | |
| 8,926,693 B2 | 1/2015 | Duffy et al. | |
| 9,101,506 B2 | 8/2015 | Arbefeuille et al. | |
| 9,259,336 B2 | 2/2016 | Schaeffer et al. | |
| 9,358,142 B2 | 6/2016 | Johnson | |
| 9,364,314 B2 | 6/2016 | Berra et al. | |
| 9,375,308 B2 | 6/2016 | Norris | |
| 9,439,751 B2 | 9/2016 | White et al. | |
| 9,592,112 B2 | 3/2017 | Arbefeuille et al. | |
| 9,770,322 B2 | 9/2017 | Burkart et al. | |
| 9,827,123 B2 | 11/2017 | Arbefeuille et al. | |
| 9,861,503 B2 | 1/2018 | Barthold et al. | |
| 9,877,857 B2 | 1/2018 | Arbefeuille et al. | |
| 9,913,743 B2 | 3/2018 | Arbefeuille et al. | |
| 10,005,269 B2 | 6/2018 | Hall et al. | |
| 10,080,674 B2 | 9/2018 | Yuan et al. | |
| 10,105,248 B2 | 10/2018 | Berra et al. | |
| 10,299,951 B2 | 5/2019 | Arbefeuille et al. | |
| 10,390,930 B2 | 8/2019 | Arbefeuille et al. | |
| 10,485,684 B2 | 11/2019 | Marmur et al. | |
| 10,617,542 B2 | 4/2020 | Chakfe et al. | |
| 10,898,357 B2 | 1/2021 | Arbefeuille et al. | |
| 10,987,235 B2 | 4/2021 | Eubanks et al. | |
| 10,987,873 B2 | 4/2021 | Moldave et al. | |
| 11,000,359 B2 | 5/2021 | Torrance et al. | |
| 2002/0062133 A1 | 5/2002 | Gilson et al. | |
| 2002/0177890 A1 | 11/2002 | Lenker | |
| 2002/0188344 A1 | 12/2002 | Bolea et al. | |
| 2002/0193872 A1 | 12/2002 | Trout et al. | |
| 2004/0059406 A1 | 3/2004 | Cully et al. | |
| 2004/0073289 A1 | 4/2004 | Hartley | |
| 2005/0102021 A1 | 5/2005 | Osborne | |
| 2005/0119722 A1 | 6/2005 | Styrc et al. | |
| 2005/0131518 A1 | 6/2005 | Hartley et al. | |
| 2005/0131519 A1 | 6/2005 | Hartley | |
| 2005/0131523 A1 | 6/2005 | Bashiri et al. | |
| 2006/0155359 A1 | 7/2006 | Watson | |
| 2007/0055360 A1 | 3/2007 | Hanson et al. | |
| 2007/0135904 A1 | 6/2007 | Eidenschink et al. | |
| 2007/0213805 A1 | 9/2007 | Schaeffer et al. | |
| 2008/0091260 A1 | 4/2008 | Pomeranz et al. | |
| 2008/0132988 A1 | 6/2008 | Jordan | |
| 2008/0269867 A1 | 10/2008 | Johnson | |
| 2009/0043377 A1 | 2/2009 | Greenberg et al. | |
| 2009/0248135 A1 | 10/2009 | Bruszewski et al. | |
| 2010/0316830 A1 | 12/2010 | Hartley et al. | |
| 2011/0190862 A1 | 8/2011 | Bashiri et al. | |
| 2011/0270378 A1 | 11/2011 | Bruszewski et al. | |
| 2012/0035714 A1 | 2/2012 | Ducke et al. | |
| 2012/0221096 A1 | 8/2012 | Roeder et al. | |
| 2012/0271401 A1 | 10/2012 | Bruszewski et al. | |
| 2012/0296360 A1 | 11/2012 | Norris et al. | |
| 2013/0116773 A1 | 5/2013 | Roeder et al. | |
| 2013/0116775 A1 | 5/2013 | Roeder et al. | |
| 2013/0282102 A1 * | 10/2013 | Peterson | A61F 2/07 623/1.13 |
| 2013/0289713 A1 | 10/2013 | Pearson et al. | |
| 2014/0046428 A1 | 2/2014 | Cragg et al. | |
| 2015/0105819 A1 | 4/2015 | Becking et al. | |
| 2015/0202065 A1 | 7/2015 | Shalev et al. | |
| 2015/0335452 A1 | 11/2015 | Rao et al. | |
| 2016/0100969 A1 | 4/2016 | Lesmeister et al. | |
| 2016/0184078 A1 | 6/2016 | Choubey et al. | |
| 2016/0199207 A1 | 7/2016 | Treacy et al. | |
| 2016/0302950 A1 | 10/2016 | Marmur et al. | |
| 2017/0281382 A1 | 10/2017 | Lostetter et al. | |
| 2018/0153680 A1 | 6/2018 | Greenberg et al. | |
| 2018/0296374 A1 | 10/2018 | Chakfe et al. | |
| 2019/0231514 A1 | 8/2019 | Arbefeuille | |
| 2019/0231568 A1 | 8/2019 | Garcia | |
| 2019/0231571 A1 | 8/2019 | Lostetter | |
| 2019/0247178 A1 | 8/2019 | Arbefeuille | |
| 2019/0247179 A1 | 8/2019 | Lostetter | |
| 2019/0247213 A1 | 8/2019 | Lostetter | |
| 2019/0269497 A1 | 9/2019 | Arbefeuille | |
| 2019/0269498 A1 | 9/2019 | Arbefeuille et al. | |
| 2019/0269537 A1 | 9/2019 | Arbefeuille | |
| 2019/0282355 A1 | 9/2019 | Lostetter | |
| 2019/0321207 A1 | 10/2019 | Arbefeuille et al. | |
| 2019/0328556 A1 | 10/2019 | Eubanks et al. | |
| 2020/0352700 A1 | 11/2020 | Torrance et al. | |
| 2021/0236262 A1 | 8/2021 | Torrance et al. | |

FOREIGN PATENT DOCUMENTS

| | | | |
|---|---|---|---|
| EP | 1847236 A2 | 10/2007 | |
| EP | 2471498 A1 | 7/2012 | |
| EP | 2735283 A1 | 5/2014 | |
| EP | 2740440 A2 | 6/2014 | |
| EP | 2745812 A1 | 6/2014 | |
| EP | 2745813 A1 | 6/2014 | |
| EP | 2749250 A1 | 7/2014 | |
| EP | 2749251 A1 | 7/2014 | |
| EP | 2606851 B1 | 11/2015 | |
| EP | 3040054 A1 | 7/2016 | |
| EP | 3068339 A1 | 9/2016 | |
| EP | 3078349 A1 | 10/2016 | |
| EP | 3146993 A1 | 3/2017 | |
| EP | 3272319 A1 | 1/2018 | |
| FR | 3042702 A1 * | 4/2017 | A61F 2/90 |
| GB | 2464978 A | 5/2010 | |
| WO | WO-97/48350 A1 | 12/1997 | |
| WO | WO-99/29262 A1 | 6/1999 | |
| WO | WO-99/34749 A1 | 7/1999 | |
| WO | WO-01/60285 A1 | 8/2001 | |
| WO | WO-03/099108 A2 | 12/2003 | |
| WO | WO-2005/034809 A1 | 4/2005 | |
| WO | WO-2005/034810 A1 | 4/2005 | |
| WO | WO-2009/148594 A1 | 12/2009 | |
| WO | WO-2010/024867 A1 | 3/2010 | |
| WO | WO-2010/024880 A1 | 3/2010 | |
| WO | WO-2010/030370 A1 | 3/2010 | |
| WO | WO-2010/127040 A1 | 11/2010 | |
| WO | WO-2012/116368 A2 | 8/2012 | |
| WO | WO-2014/149022 A1 | 9/2014 | |
| WO | WO-2015/070792 A1 | 5/2015 | |
| WO | WO-2016/122862 A1 | 8/2016 | |
| WO | WO-2018/026768 A1 | 2/2018 | |

OTHER PUBLICATIONS

International Search Report and Written Opinion for International Application No. PCT/US2018/019352 dated May 7, 2018.

* cited by examiner

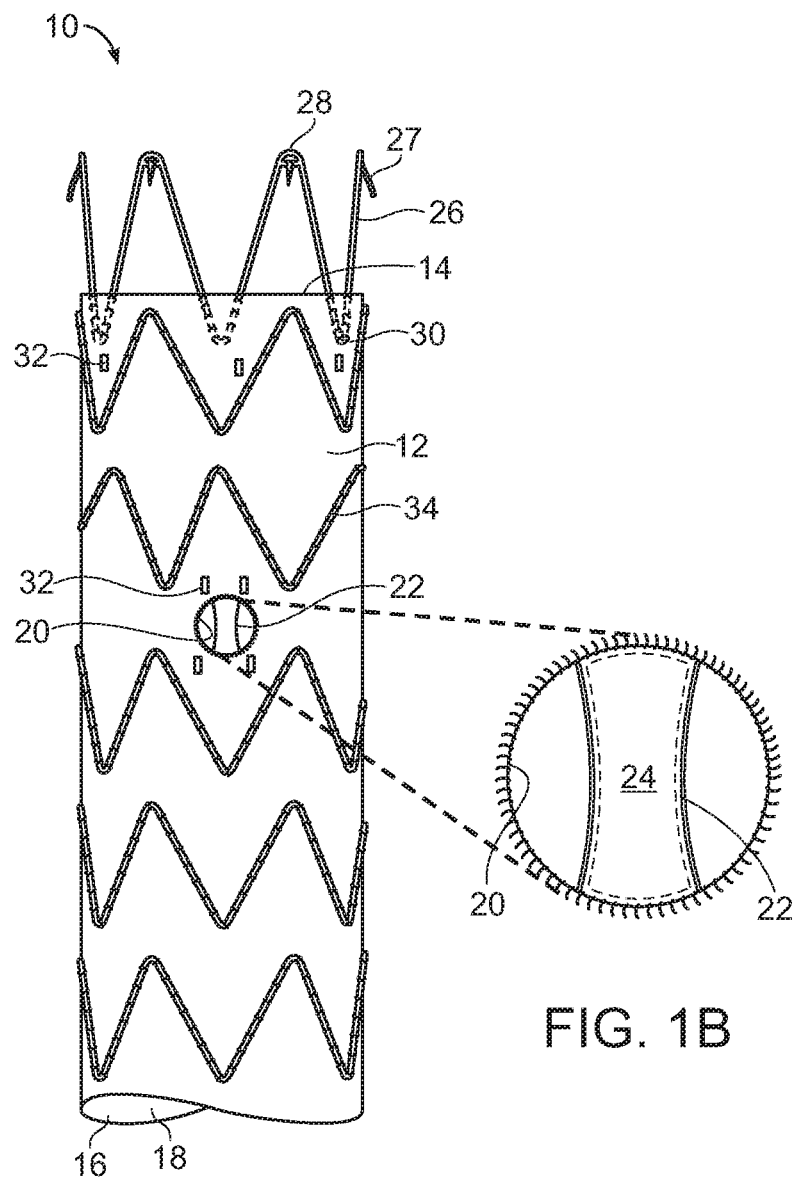
FIG. 1A
FIG. 1B
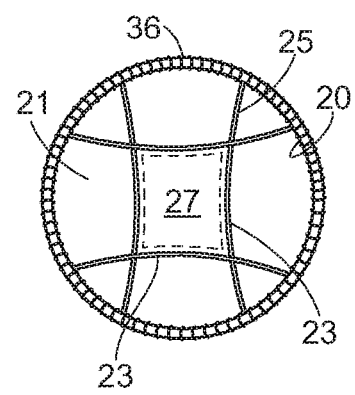
FIG. 2

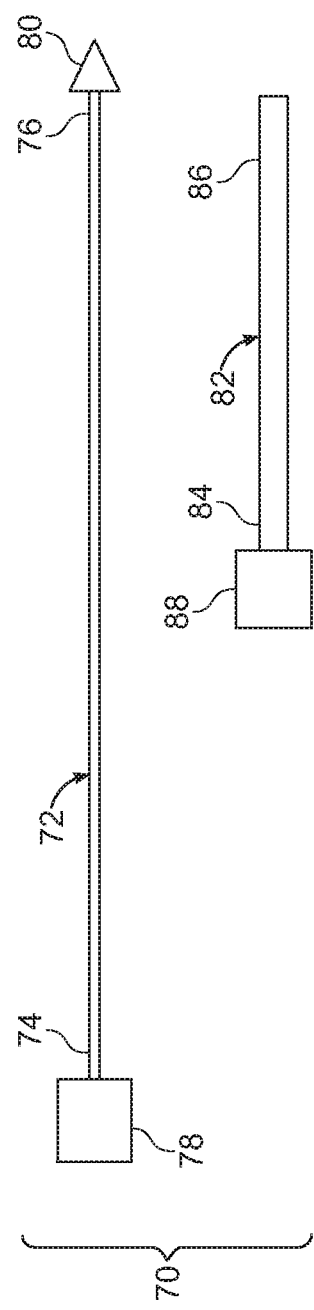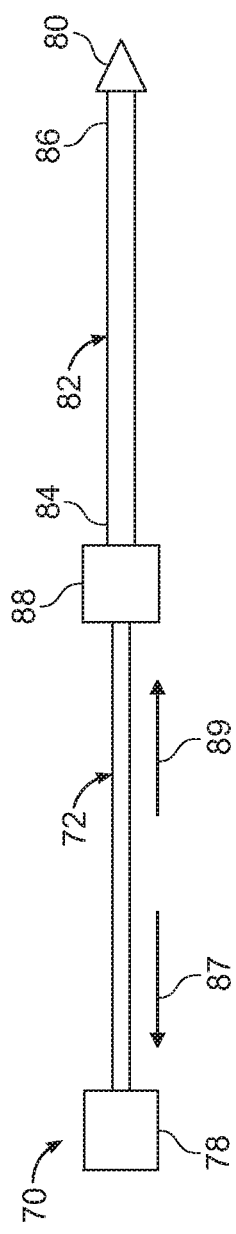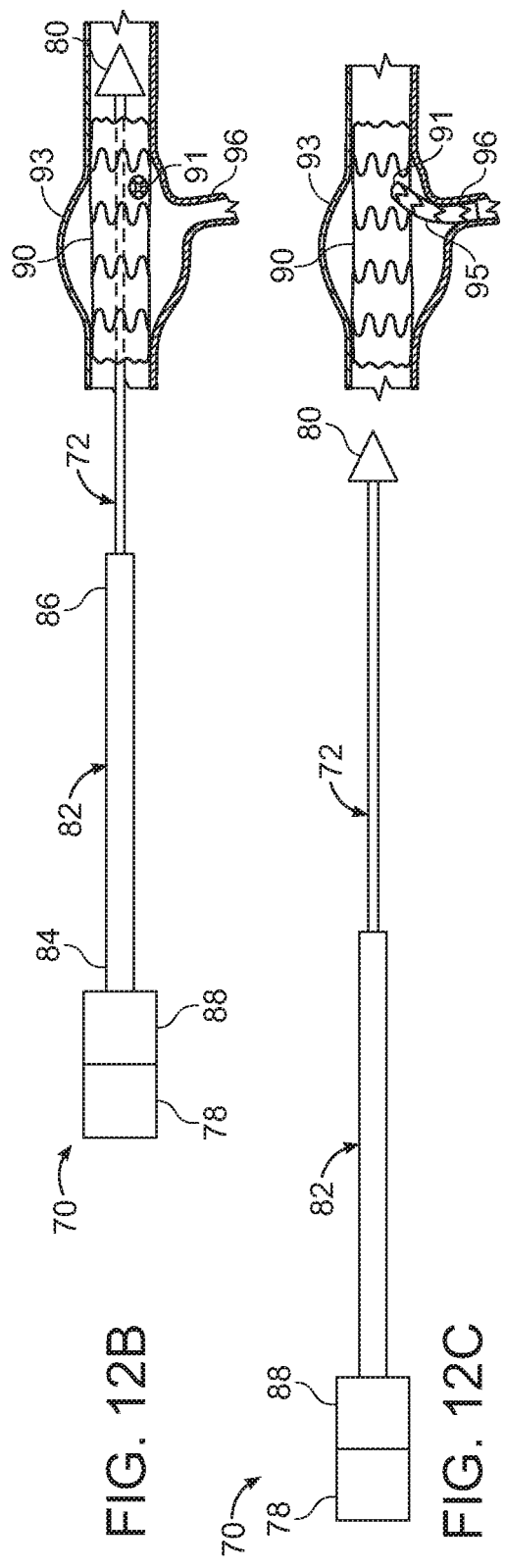
FIG. 11 (PRIOR ART)
FIG. 12A
FIG. 12B
FIG. 12C

STENT GRAFT WITH FENESTRATION LOCK AND METHODS OF USE

RELATED APPLICATION

This application is a continuation of International Application No. PCT/US2018/019352, which designated the United States and was filed on Feb. 23, 2018, published in English, which claims the benefit of U.S. Provisional Application No. 62/463,054, filed on Feb. 24, 2017. The entire teachings of the above applications are incorporated herein by reference.

BACKGROUND

Fenestrated endovascular aortic repair (FEVAR) is a minimally invasive procedure to treat arterial aneurysms that span blood vessels that supply blood to vital organs including the kidneys, intestine and liver. Endovascular grafts employed in FEVAR define fenestrations for insertion of branch prostheses that serve as passageways for blood flow through arterial branches to vital organs following implantation of the endovascular graft. Maximizing blood flow to vital organs and minimizing endoleaks following repair of arterial aneurysms with fenestrated vascular prostheses, such as juxtarenal aortic aneurysms and short-neck abdominal aortic aneurysms, present medical challenges that must be overcome if more invasive surgical intervention is to be avoided.

Therefore, a need exits for new and improved endovascular repair devices and methods of their use to treat arterial pathologies, such as juxtarenal and short-neck abdominal aortic aneurysms.

SUMMARY

The present invention relates to stent grafts for use in treating and repairing arterial vascular damage, such as vascular damage associated with arterial aneurysms including juxtarenal aortic aneurysms and short-neck abdominal aortic aneurysms, having associated arterial branches supplying blood to vital organs and tissues.

In one embodiment, the invention is a stent graft that includes a luminal graft component having a proximal open end, a distal open end, and defining a main lumen extending from the proximal open end to the distal open end. The luminal graft component defines at least one fenestration. At least one ligature traverses the at least one fenestration, wherein the ligature, along or in combination with the luminal graft component, constitutes a fenestration lock at the fenestration, whereby a branch prosthesis can be secured by the fenestration lock.

In another embodiment, the invention is a method for treating an arterial aneurysm that includes delivering a stent graft through an artery to an aneurysm of a patient, the aneurysm spanning a region of an artery that spans an associated arterial branch. The stent graft includes a luminal graft component having a proximal open end, a distal open end, and a main lumen extending from the proximal open end to the distal open end, and wherein the luminal graft component defines at least one fenestration. At least one ligature traverses the fenestration, the ligature alone or in combination with the luminal graft component, constitutes a fenestration lock at the fenestration, whereby a proximal end or a distal end of a branch prosthesis can be secured by the fenestration lock. The fenestration is substantially aligned with the associated arterial branch at the aneurysm site of the patient and then the stent graft is at least partially released from a delivery device. At least one branch prosthesis is delivered through the proximal open end or the distal open end of the luminal graft component of the stent graft, and through the opening and to the associated arterial branch, thereby treating the arterial aneurysm.

The vascular prostheses of the invention have several advantages by, for example, providing the surgeon with increased flexibility to accommodate anatomical variations in the size of arterial branches at an aneurysm. Specifically, the fenestration lock in a luminal graft can better secure a branch prosthesis during implantation. The vascular prostheses of the invention also have the additional advantage of improving a seal between a fenestration of the stent graft of the invention and a branch prosthesis by limiting motion of the branch prostheses, following insertion of the branch prosthesis through the fenestration, thereby significantly reducing the incidence and severity of endoleaks and resulting complications.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1A is a side view of one embodiment of a stent graft of the invention.

FIG. 1B is a detail of a fenestration lock of the stent graft of FIG. 1A.

FIG. 2 is a side view of a fenestration lock of another embodiment of a stent graft of the invention.

FIG. 11 is an exploded view of one embodiment of a (prior art) delivery device for use in implanting a stent graft of the invention.

FIG. 12A is a side view of the delivery device of FIG. 11, and containing a stent graft of the invention (not shown) loaded within an introducer sheath of the delivery device.

FIG. 12B is a side view of the delivery device of FIG. 12A, following retraction of an introducer sheath component of the delivery device to expose a stent graft of the invention or a branch prosthesis during delivery to an aneurysm site.

FIG. 12C is a side view of the delivery device and the stent graft of FIG. 12B after retraction of the delivery device from the stent graft of the invention or the branch prosthesis, thereby completing implantation of the prosthesis following removal of the delivery device from the stent graft.

FIG. 13B is a detail of a fenestration lock of the stent graft of FIG. 13A.

DETAILED DESCRIPTION OF THE INVENTION

Figure 3:
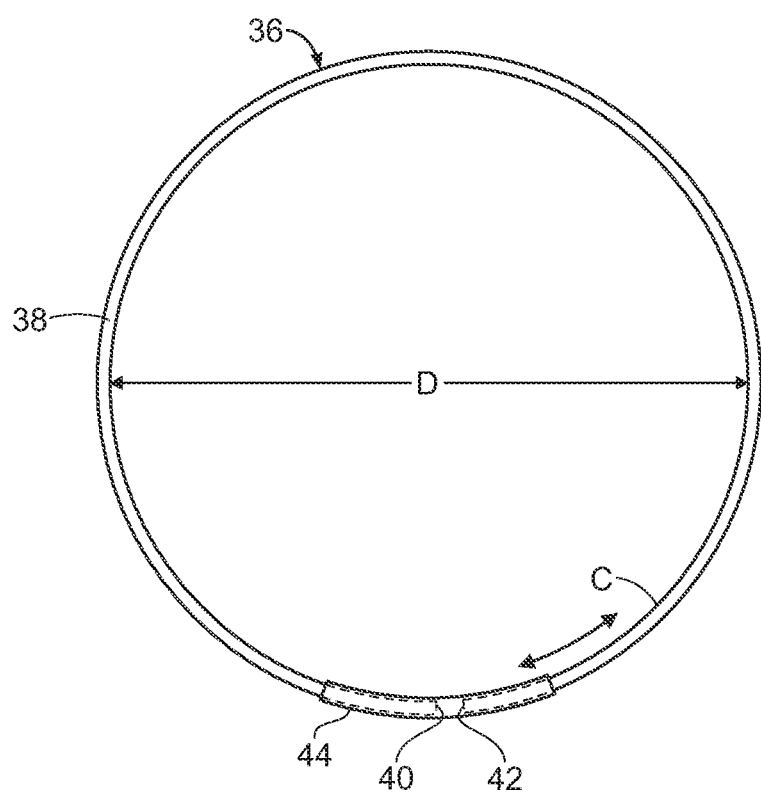
FIG. 3 is a perspective view of a fenestration ring that can be included as a component of a stent graft of the invention.
Figure 4:
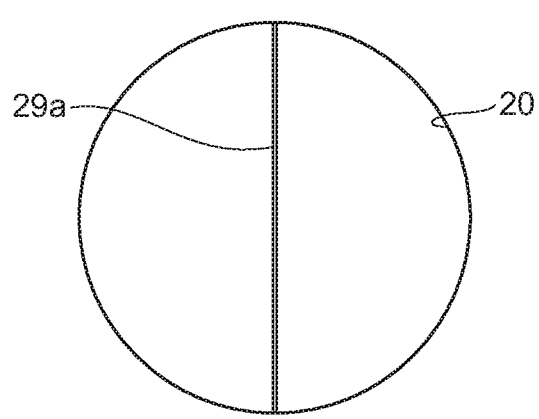
FIG. 4 is a side view of a fenestration lock of another embodiment of a stent graft of the invention.
Figure 5:
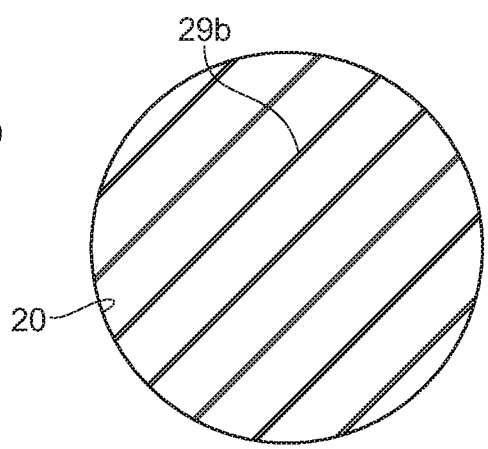
FIG. 5 is a side view of a fenestration lock of a further embodiment of a stent graft of the invention.
Figure 6:
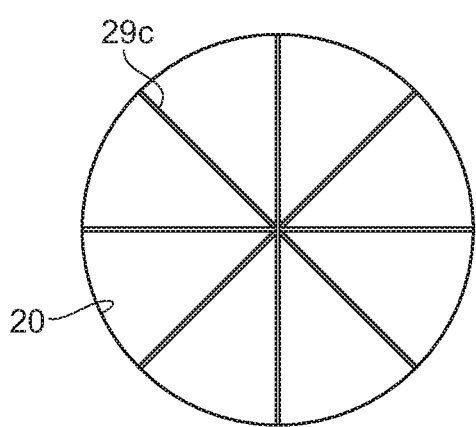
FIG. 6 is a side view of a fenestration lock of yet another embodiment of a stent graft of the invention.
Figure 7:
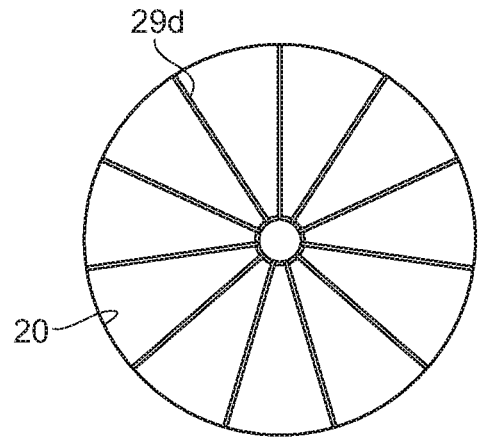
FIG. 7 is a side view of a fenestration lock of an additional embodiment of a stent graft of the invention.
Figure 8:
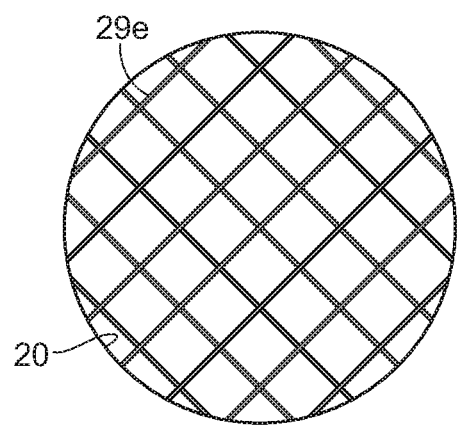
FIG. 8 is a side view of a fenestration lock of still another embodiment of a stent graft of the invention.

The invention is generally directed to stent graft and methods for treating and repairing aortic vascular damage, such as vascular damage associated with an aortic aneurysm in regions of the aorta having arterial branches to vital organs and tissues, such as juxtarenal aortic aneurysms and short-neck abdominal aortic aneurysms.

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A description of example embodiments of the invention follows.

When reference is made herein to a prosthesis, also referred to herein as a "stent graft," "stent graft prosthesis," or "stent graft," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient. A "longitudinal axis," as that term is defined herein, means an axis along a lengthwise direction of a body that also passes through a center of gravity of the body.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

In an embodiment, the stent graft is shown in FIG. 1A. Stent graft 10 includes luminal graft component 12 having proximal open end 14, distal open end 16, and defining lumen 18 extending from the proximal open end 14 to distal open end 16. Luminal graft component 12 defining at least one fenestration 20. Luminal graft component 12 is made from a suitable material, such as is known to one of skill in the art, including, for example, polytetrafluoroethylene (PTFE), such as ePTFE, and polyethylene terephthate (PET), such as woven polyester.

Ligatures 22 traverse fenestration 20 of luminal graft component 12 to thereby at least partially define opening 24, within fenestration 20. As shown later, a branch prosthesis can be secured within fenestration 20 by plurality of ligatures 22, ligatures 22 and a portion of the periphery of fenestration 20 thereby constituting a fenestration lock.

Ligatures 22 are affixed to luminal graft component 12 and fenestration 20 by a suitable method, such as is known to those skilled in the art. Examples of a suitable method include use of sutures or a biocompatible adhesive. Ligatures 22 are fabricated of a suitable material such as is known in the art, including, for example, at least one member selected from the group consisting of sutures, cloth, metal, and an elastic material, such as a biocompatible rubber band or latex. Examples of suitable sutures include sutures fabricated of at least one member of the group consisting of PTFE, ePTFE, polyglycolic acid, polylactic acid, monocryl and polydioxane, non-absorbable nylon, polyester, polyvinylidene difluoride (PVDF) and polypropylene. Suitable rubber bands can include, for example, rubber bands formed of natural rubber or a synthetic rubber. Metal can include wires, such as an elastic material or shape memory alloy. Metal ligatures can include a shape memory alloy, such as nitinol, and stainless steel.

Optionally, stent graft 10 includes radially expanding bare stent 26 having proximal apices 28 and distal apices 30. Proximal apices 28 extend proximally beyond proximal open end 14 of luminal graft component 12. In an embodiment, proximal apices 28 include a fixation component, such as at least one barb 27. Distal apices 30 of bare stent 26 are fixed to proximal open end 14 of luminal graft component 12.

Suitable radiopaque markers 32, such as those known to those skilled in the art, are secured, such as by suturing or use of biocompatible adhesive, to at least one of proximal open end 14, distal open end 16, the perimeter of fenestration 20 of luminal graft component 12, and fenestration lock 24, which is constituted by ligatures 22 and a portion of the perimeter of fenestration 20. Radiopaque markers 32, in one embodiment, are incorporated into ligatures 22. In an embodiment, ligatures 22, radiopaque markers 32 and ring 36 (described in detail below) include a radiopaque material, such as at least one radiopacifier selected from the group consisting of barium sulfate, bismuth, tungsten, platinum, platinum-iridium, tantalum and tantalum-tungsten.

Stent graft 10 includes plurality of stents 34 distributed longitudinally along luminal graft component 12. Stents 34 are formed from a suitable material, such as is known to those skilled in the art, including, for example, stainless steel or a shape-memory alloy, such as Nitinol. Stents 34 are fixed to luminal graft component by suitable means known to those skilled in the art, such as by suturing or affixation by employment of biocompatible adhesive.

As shown in detail in FIG. 1B, ligatures 22 of stent graft 10 are substantially parallel to each other. Ligatures 22 are secured at one or more points to luminal graft component 12 at perimeter of fenestration 20 by one or more suitable methods, such as is known to one of skill in the art. Examples of such suitable methods include suturing along intermittent or continuous lengths (not shown), or along the entire length of the perimeter of fenestration 20 to thereby constitute fenestration lock 24. Suitable suture materials for securing plurality of sutures include sutures fabricated of PTFE, ePTFE, polyglycolic acid, polylactic acid, monocryl and polydioxane, non-absorbable nylon, polyester, polyvinylidene difluoride (PVDF) and polypropylene, staples, biocompatible adhesive, or other suitable material as is known to one skilled in the art. As shown in FIG. 2, in another embodiment, a stent graft defines fenestration 21 and includes ligatures 23 that are substantially parallel to each other and ligatures 25 that are substantially perpendicular to the substantially parallel ligatures 22, to thereby constitute fenestration lock 27. Alternative embodiments of a fenestration lock of the stent graft of the invention are shown in FIGS. 4, 5, 6, 7, and 8, that include examples of suitable ligature configurations 29a, 29b, 29c, 29d, and 29e, respectively. Each of ligature configurations 29a, 29b, 29c, 29d, and 29e constitutes an example of a fenestration lock.

Returning to FIG. 2, the periphery of fenestration 20 can be encompassed by ring 36, which extends about the perimeter of fenestration 20. In one embodiment, ring 36 is a self-expanding stent, and is formed of a suitable material, such as stainless steel, a suitable polymer, or a shape memory alloy, such as Nitinol. In one embodiment, shown in FIG. 3, ring 36 includes main component 38 that defines ends 40,42 that are linked by connecting component 44 that is fixed or slideably engaged with either or both ends. Examples of suitable rings are further described in "Vascular Prosthesis with Moveable Fenestration and Method of Use," filed Feb. 23, 2018, by Samuel Arbefeuille, the teachings of which are incorporated herein by reference in their entirety.

Figure 9:
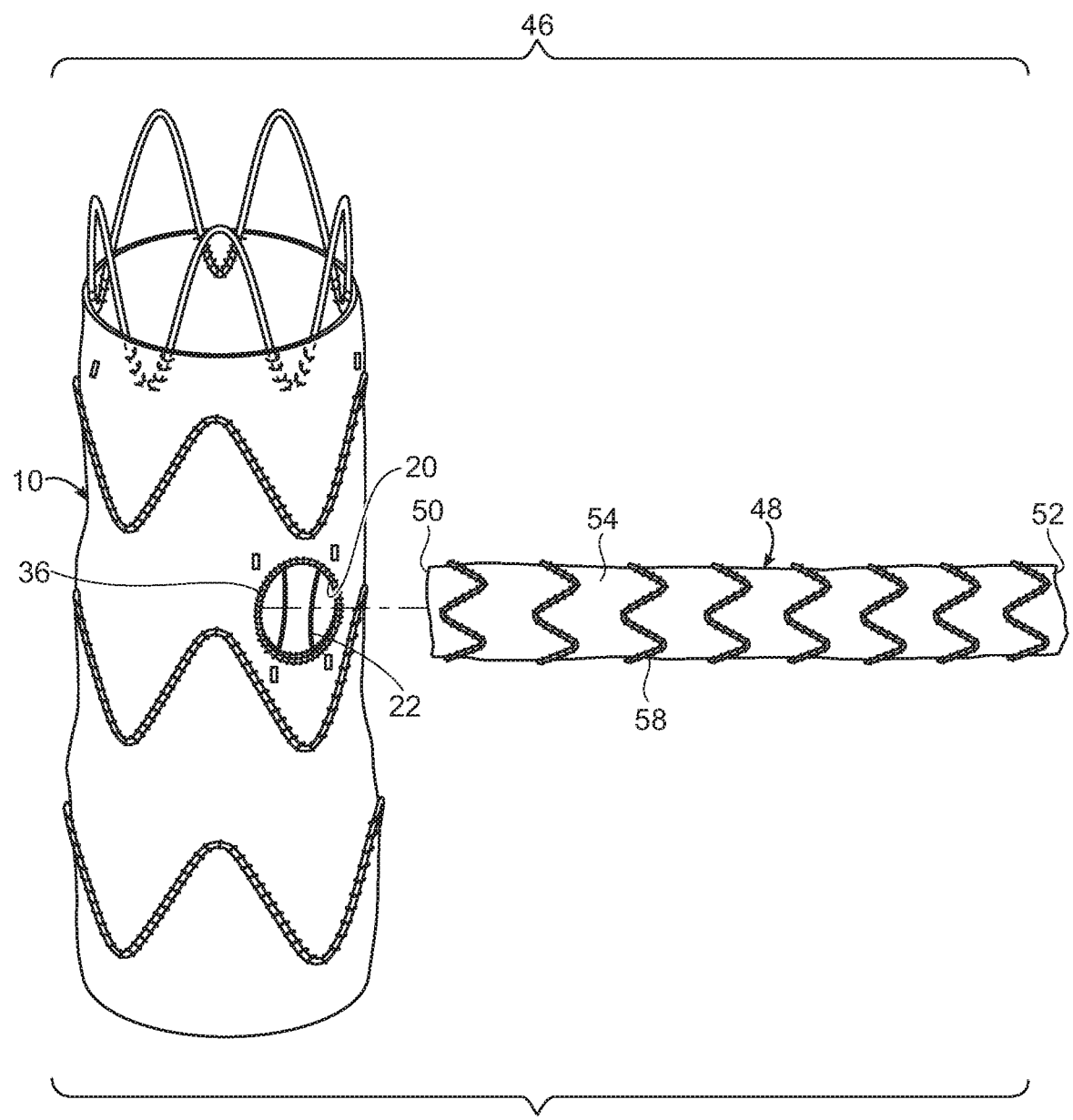
FIG. 9 is an exploded side view of one embodiment of a stent graft assembly of the invention.
Figure 10:
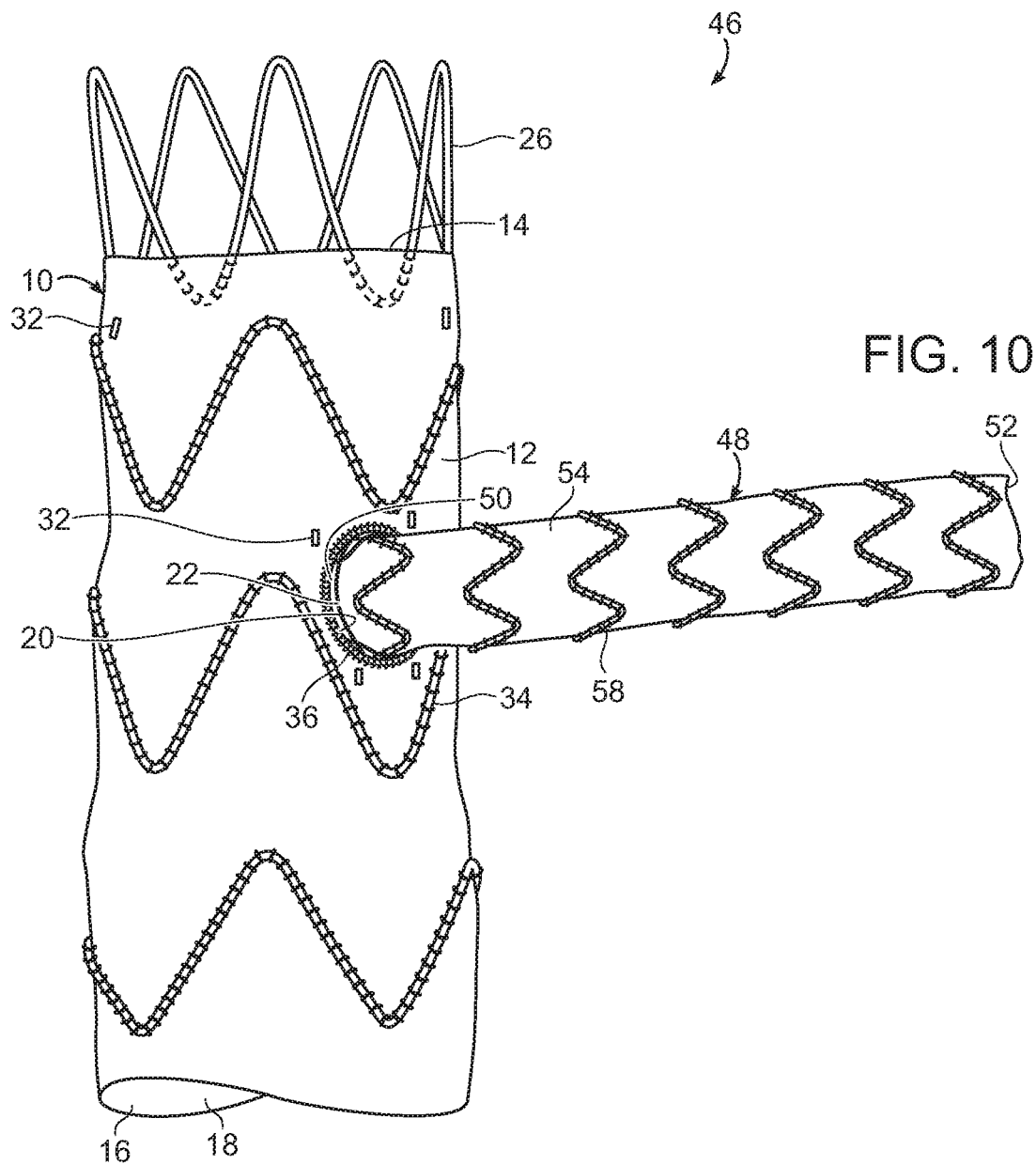
FIG. 10 is a side view of the assembled stent graft of the invention and (prior art) branch prosthesis of FIG. 9, following delivery through the fenestration lock of the branch prosthesis.

FIG. 9 is an exploded side view of a stent graft assembly 46 of the invention, including stent graft 10, as represented in FIG. 1A, and a suitable branch prosthesis 48. Branch prosthesis 48 includes proximal end 50, distal end 52, luminal graft component 54 defining a lumen, and stents 58 extending along luminal graft component 54. FIG. 10 is a side view of assembled stent graft assembly 46 shown in FIG. 9, following delivery of branch prosthesis through fenestration lock 24 of stent graft 10. Distal end 52 of branch prosthesis 48 is positioned through fenestration lock 24 which is constituted, at least in part, of ligatures 22 or, alternatively by ligatures 22 and a portion of periphery of fenestration 20, as shown in FIG. 1B. Fenestration lock 24 locks branch prosthesis 48 upon implantation of branch prosthesis 48 within fenestration lock 24, such as by at least one of reversible or elastic accommodation of a diameter of branch prosthesis 48, or by constriction of branch prosthesis 48 during radial expansion of branch prosthesis 48 after delivery through fenestration lock.

FIG. 11 is an exploded side view of a prior art delivery device suitable for delivering a stent graft of the invention. As can be seen in FIG. 11, prior art delivery device 70 includes guidewire catheter 72 having proximal end 74 and distal end 76. Proximal handle 78 is fixed to proximal end 74 and nose cone 80 is fixed to distal end 76. Introducer sheath 82 has proximal end 84 and distal end 86. Distal handle 88 is fixed to proximal end 84. Introducer sheath 82 can be rigid or flexible.

FIG. 12A is a side view of the prior art delivery device 70 when assembled and loaded with a stent graft of the invention. As can be seen therein, introducer sheath 82 and distal handle 88 extend around guidewire catheter 72. Although not shown, stent graft 10 of the invention is held in a radially constricted position around guidewire catheter 72 and within introducer sheath 82. In a method of the invention, stent graft 90 is implanted at aneurysm 93 by advancing delivery device 70 within an artery of a patient until stent graft 70 spans aneurysm 93. As can be seen in the embodiment shown in FIGS. 12A through 12C, with reference to FIG. 12B, distal handle 88 is then retracted in the direction of arrow 87 along guidewire catheter 72 and toward proximal handle 78, thereby retracting introducer sheath 82 from around stent graft 90 with at least one fenestration 91. In another embodiment, not shown, delivery device 70 can be advanced in an artery until introducer sheath 82 and stent graft 90 within introducer sheath 82 are distal to aneurysm 93, whereby proximal handle 98 and stent graft 90, which is attached to guidewire catheter 72, are advanced in the direction of arrow 89 to thereby direct stent graft 90 from introducer sheath 82 and span aneurysm 93. Stent graft 70 is released from its constricted position, and radially expands to a released position, such as by use of a balloon catheter, or by use self-expanding radial stents, as is known in the art, and is thereby deployed at the aneurysm site. Delivery device 70 thereafter is removed from the patient, as shown in FIG. 12C, thereby completing implantation of the stent graft and treatment of the aortic aneurysm. The same or a similar delivery device can be employed to deliver or implant proximal end branch prosthesis 95 through fenestration 91 of stent graft 90 of the invention and distal end of branch prosthesis into arterial branch 96. It is to be understood that, alternatively, other suitable types of aortic prosthesis delivery devices, such as are known in the art, can be employed.

Figure 13A:
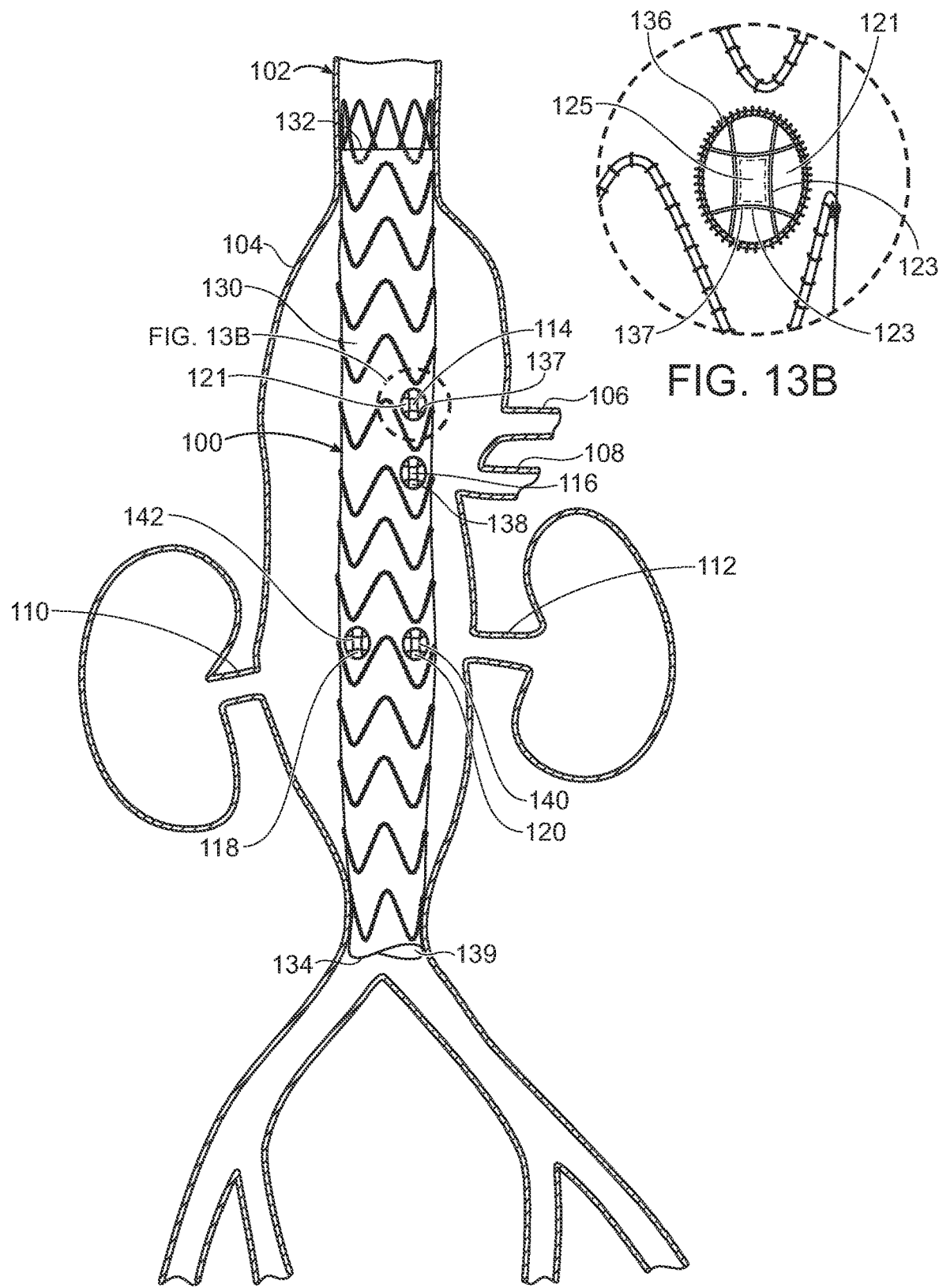
FIG. 13A is a side view of another embodiment of the stent graft of the invention after implantation at an aneurysm site of a patient.

In another embodiment of a method of the invention, described with reference to FIG. 13A, stent graft 100 is delivered by use of a suitable delivery device, as described above, through artery 102 to aneurysm 104 spanning a region of aorta 102 that includes at least one arterial branch, such as at least one of celiac artery 106, superior mesenteric artery 108, right renal artery 110 and left renal artery 112. Stent graft 100 is radially and releasably constrained by a suitable stent graft delivery device, as shown in FIG. 12A. FIG. 13B, which is a detail of fenestration 114 of FIG. 13A, shows plurality of ligatures 121, 123 of fenestration 114 that is encompassed by ring 136. As shown in FIG. 13B, plurality of ligatures 121, 123 span fenestration 114 to thereby constitute fenestration lock 125. Stent graft 100 is rotated about a longitudinal axis to approximately align fenestrations 114, 116, 118, 120 with corresponding arterial branches 106, 108, 110, 112 of aorta 102 at aneurysm site 104. Stent graft 100 is then released from stent graft delivery device.

Stent graft 100 includes luminal graft component 130 that has proximal end opening 132, distal end opening 134, and defines main lumen 139.

Figure 14:
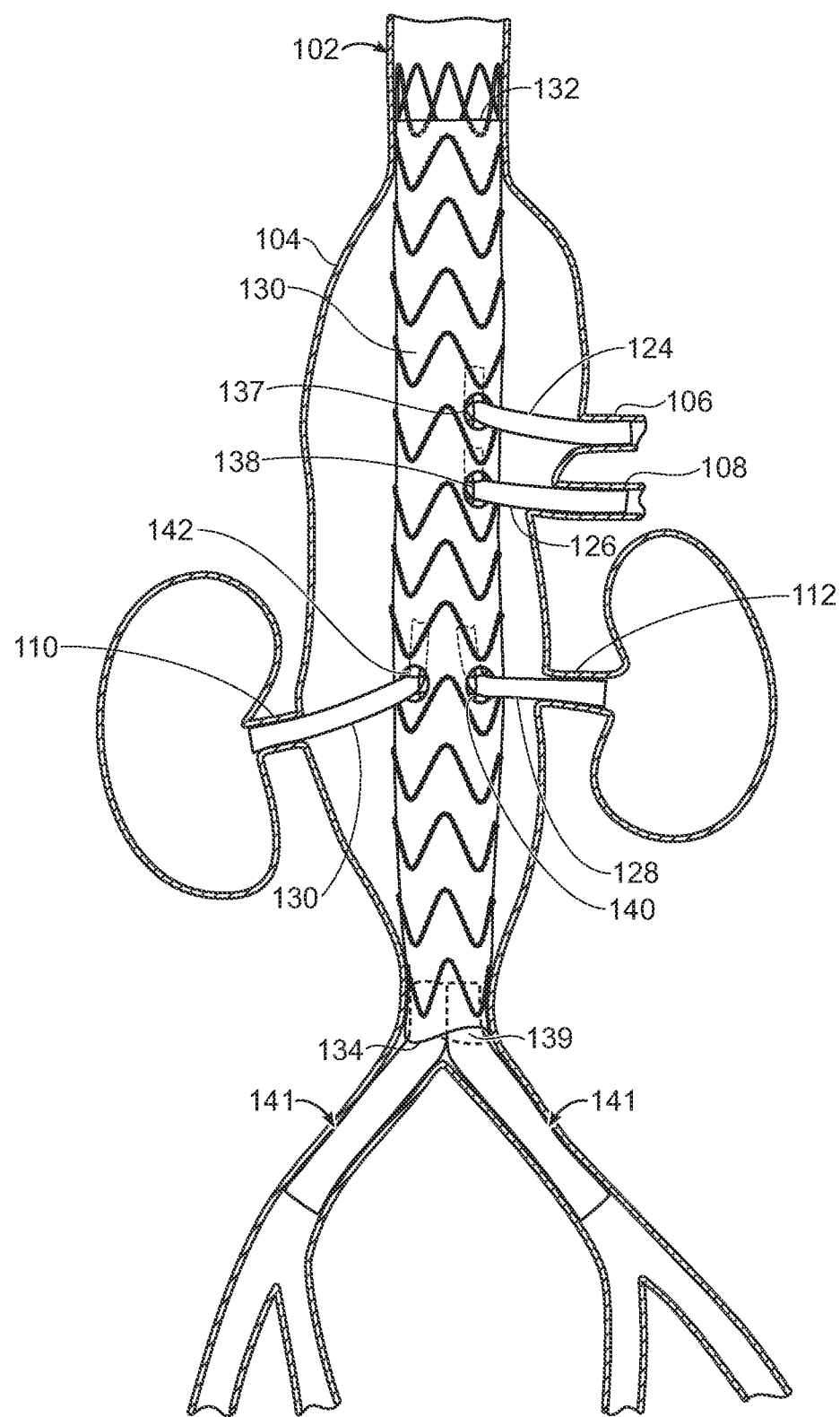
FIG. 14 is a side view of the implanted stent graft of FIG. 13A following implantation of a branch prostheses.

Each branch prosthesis 124, 126, 128, 130 is delivered by a respective branch prosthesis delivery device, such as shown in FIGS. 11 and 12A through 12C through proximal opening 132 or distal opening 134 into the main lumen 139 of the luminal graft component 130, as shown in FIG. 14. A distal end of each of branch prosthesis 122, 124, 126, 128 is then delivered through respective fenestration lock 137, 138, 140, 142 at each respective fenestration 114, 116, 118, 120 and into the respective branch 106, 108, 110, 112 of the aorta and secured therein. Each branch prosthesis 122, 124, 126, 128 is then released from the respective branch prosthesis delivery device, and each branch prosthesis 122, 124, 126, 128 expands radially from a constricted position to an expanded position, such as by use of a suitable balloon catheter, or a self-expanding radial stents at the stent graft. Expansion of each branch prosthesis, 122, 124, 126, 128 at each respective opening presses against the ligatures that define each fenestration lock 137, 138, 140, 142, thereby locking the proximal end of each branch prosthesis at the respective fenestration lock. Stent graft 100 is then removed from the patient, thereby completing implantation and treatment of the aortic aneurysm. In an embodiment, additional branch prosthesis 141 can be implanted into distal end of vascular prostheses of the invention.

Although not shown, the distal end of the vascular prostheses of the invention can be bifurcated and additional branch prostheses can be implanted into the distal end of the bifurcated stent graft.

Vascular prostheses of the invention can be implanted, for example, by transfemoral access. Additional vascular repair devices that are directed into the vascular prostheses of the invention can be implanted, for example, by supraaortic vessel access (e.g., through the brachial artery), or by transfemoral access or access from some other branch or branches of major blood vessels including peripheral blood vessels.

The teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712; 9,827,123, 9,877,857, 9,907,686; U.S. patent application Ser. Nos. 14/575,673; 15/166,818; 15/167,055; 14/272,818; 14/861,479; 15/478,424; 15/478,737; 15/587,664; 15/604,032; 15/672,404; 15/816,772; 15/839,272; 15/417,467; PCT/US2017/025844; PCT/US2017/025849; PCT/US2017/025912; PCT/US2017/034223 and PCT/US2017/046062, are also incorporated by reference in their entirety.

The relevant teachings of the "Delivery System For Radially Constricting a Stent Graft and Method of Use," by Eduardo Alejandro Garcia, filed on Feb. 23, 2018; "System and Method to Radially Constrict Stent Graft," by Samuel Arbefeuille, filed on Feb. 23, 2018; "Delivery System and Method to Radially Constrict a Stent Graft," by Timothy Lostetter, filed on Feb. 23, 2018; "Vascular Prosthesis with Moveable Fenestration and Method of Use," by Samuel Arbefeuille, filed on Feb. 23, 2018; "Stent Graft Delivery System with Constricted Sheath and Method of Use," by Timothy Lostetter, filed on Feb. 23, 2018; "Stent Graft, Delivery System and Methods of Use," by Samuel Arbefeuille and Nico Bahar, filed on Feb. 23, 2018; "Vascular Prosthesis with Crimped Adapter and Methods of Use," by Samuel Arbefeuille, filed on Feb. 23, 2018; "Radially Adjustable Stent Graft Delivery System and Method of Use," by Samuel Arbefeuille, Eduardo Alejandro Garcia and Scott L. Rush, filed on Feb. 23, 2018; "Vascular Prosthesis with Fenestration Ring and Methods of Use," by Timothy Lostetter, filed on Feb. 23, 2018; "Distal Torque Component, Delivery System and Method of Using Same," by Samuel Arbefeuille, filed on Feb. 23, 2018, are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A stent graft, comprising:
   a) a luminal graft component having a proximal open end, a distal open end, and defining a main lumen extending from the proximal open end to the distal open end, the luminal graft component defining at least one fenestration;
   b) at least one ligature completely traversing the at least one fenestration, the at least one ligature, in combination with the luminal graft component, constituting at least one fenestration lock at the at least one fenestration, whereby a branch prosthesis can be secured by the at least one fenestration lock; and
   c) at least one fenestration ring encompassing the at least one fenestration and fixed to the luminal graft component, the at least one fenestration ring defining a variable fenestration ring diameter, wherein the fenestration ring diameter can expand upon insertion of a branch prosthesis through the at least one fenestration ring during implantation of the branch prosthesis.

2. The stent graft of claim 1, wherein the at least one ligature is at least one member selected from the group consisting of sutures, rubber bands, latex, cloth, and metal.

3. The stent graft of claim 1, wherein the at least one ligature includes an elastic material.

4. The stent graft of claim 1, wherein the at least one ligature includes a shape memory alloy.

5. The stent graft of claim 4, wherein the shape memory alloy is Nitinol.

6. The stent graft of claim 1, wherein the at least one ligature includes at least two ligatures that are substantially parallel to each other.

7. The stent graft of claim 1, wherein the at least one ligature is a plurality of ligatures that includes ligatures that are substantially parallel to each other and ligatures that are substantially perpendicular to the substantially parallel ligatures.

8. The stent graft of claim 1, wherein the at least one ligature is a plurality of ligatures that completely form the at least one fenestration lock.

9. The stent graft of claim 1, further including a plurality of radially self-expanding stents distributed longitudinally along the luminal graft component, wherein the at least one fenestration is between two of the plurality of radially self-expanding stents.

10. The stent graft of claim 1, further including a radially self-expanding stent along the circumference of the at least one fenestration.

11. The stent graft of claim 1, further including a radially self-expanding bare stent having proximal and distal apices, the proximal apices extending beyond the proximal open end of the luminal graft component and the distal apices being affixed to the proximal open end of the luminal graft component.

12. The stent graft of claim 1, further including at least one branch prosthesis having a proximal end and a distal end, either the proximal end or the distal end of the branch prosthesis extending through the at least one fenestration lock of the luminal graft component.

13. A stent graft, comprising:
   a) a luminal graft component having a proximal open end, a distal open end, and defining a main lumen extending from the proximal open end to the distal open end, the luminal graft component defining at least one fenestration; and
   b) at least one ligature completely traversing the at least one fenestration, the at least one ligature, alone or in combination with the luminal graft component, constituting at least one fenestration lock at the at least one fenestration, whereby a branch prosthesis can be secured by the at least one fenestration lock; and
   c) at least one fenestration ring encompassing the at least one fenestration and fixed to the luminal graft component, the at least one fenestration ring defining a variable fenestration ring diameter and including a main component having two non-overlapping opposing ends, and a connecting component that bridges the two non-overlapping opposing ends to thereby complete configuration of the main component as a ring, wherein the fenestration ring diameter can expand upon insertion of a branch prosthesis through the at least one fenestration ring during implantation of the branch prosthesis.

* * * * *